United States Patent [19]
Smith et al.

[11] Patent Number: 6,147,068
[45] Date of Patent: Nov. 14, 2000

[54] LIPOPHILIC POLYAMINE ESTERS FOR THE SITE SPECIFIC DELIVERY OF NITRIC OXIDE IN PHARMACEUTICAL USE

[75] Inventors: Daniel J. Smith, Stow, Ohio; Dominick Roselle, Odenton, Md.

[73] Assignee: The University of Akron, Akron, Ohio

[21] Appl. No.: 09/157,856

[22] Filed: Sep. 21, 1998

Related U.S. Application Data

[63] Continuation-in-part of application No. 08/703,898, Aug. 27, 1996, abandoned.

[51] Int. Cl.[7] .................... A61K 31/13; A61K 31/195; C07C 229/26; C07C 243/42

[52] U.S. Cl. .................. 514/182; 514/547; 514/551; 514/611; 514/645; 552/547; 560/169; 564/113; 564/297

[58] Field of Search .................... 552/547; 560/169; 564/113, 297; 514/182, 547, 551, 611, 645

[56] References Cited

U.S. PATENT DOCUMENTS

| | | | |
|---|---|---|---|
| 5,039,705 | 8/1991 | Keefer et al. | 514/611 |
| 5,049,389 | 9/1991 | Radhakrishnan | 424/450 |
| 5,155,137 | 10/1992 | Keefer et al. | 514/611 |
| 5,185,376 | 2/1993 | Diodati et al. | 514/611 |
| 5,208,233 | 5/1993 | Keefer et al. | 514/231.8 |
| 5,266,480 | 11/1993 | Naughton et al. | 435/240.243 |
| 5,358,715 | 10/1994 | Wong et al. | 424/449 |
| 5,366,997 | 11/1994 | Keefer et al. | 514/611 |
| 5,371,089 | 12/1994 | Rattan | 514/261 |
| 5,385,937 | 1/1995 | Stamler et al. | 514/557 |
| 5,389,675 | 2/1995 | Christodoulou et al. | 514/492 |
| 5,443,950 | 8/1995 | Naughton et al. | 435/1 |
| 5,455,335 | 10/1995 | Kahne et al. | 536/5 |
| 5,525,357 | 6/1996 | Keefer et al. | 424/486 |
| 5,650,442 | 7/1997 | Mitchell et al. | 514/611 |
| 5,650,447 | 7/1997 | Keefer et al. | 514/772.4 |

OTHER PUBLICATIONS

"The Reaction of Nitrogen (II) Oxide with Diethylamine" by Drago and Paulik, Contribution from the W.A. Noyes Laboratory, University of Illinois, pp. 96–98, 1959.

"Polycondensation of ω–Aminoalkylamino Acid Esters" by Asahara, Basic Research Laboratory, Toray Industries, Inc., Japan, pp. 211–219, 1970.

"Thermal Bulk Polymerization of Cholesteryl Acrylate" by Visser et al., Twente University of Technology, Netherlands, pp. 1893–1894, 1971.

"Synthesis of Putreanine and of Spermic Acid" by Tabor and Tabor, *Methods in Enzymology*, vol. 94, pp. 418–422, 1983.

"Complexes of NO with Nucleophiles as Agents for the Controlled Biological Release of Nitric Oxide. Vasorelaxant Effects" by Maragos et al., *J. Med. Chem.*, vol. 34, pp. 3242–3247, 1991.

"The Molecule of the Year" by Koshland, Jr., *Science*, vol. 258, pp. 1861–1865, 1992.

Morrison et al., Organic Chemistry, Fifth Edition, Allyn and Bacon, Inc., New York, p. 865, 1987.

"New Nitric Oxide–Releasing Zwitterions Derived from Polyamines" by Hrabie and Klose, *J. Org. Chem.*, vol. 5c, pp. 1472–1476, 1993.

"The Surprising Life of Nitric Oxide" by Feldman et al., *C&EN*, Special Report, pp. 26–38, 1993.

"Toward the generation of No in Biological Systems. Theoretical Studies of the $N_2O_2$ Grouping" by Taylor et al., *J. Org. Chem.*, vol. 60, pp. 435–444, 1995.

"Nitric Oxide and Asthma" by Barnes, National Heart and Lung Institute, London, pp. 698–702.

"Characterization and Nitric Oxide Release Studies of Lipophilic 1–Substituted Diazen–1jum–1,2–diolates" by Roselle and Smith, *Journal of Controlled Release*, vol. 51, pp. 131–142, 1998.

"Synthesis of Lipophilic 1–Substituted Diazen–1ium–1, 2–diolates" by Roselle and Smith, *Chem. Pharm. Bull.*, 45(4), pp. 747–749, 1997.

"Secondary Amine/Nitric Oxide Complex Ions, $R_2N[N(O)NO]$ O–Functionalization Chemistry" by Saavedra et al., *J. Org. Chem.*, vol. 57, pp. 6134–6138, 1992.

*Primary Examiner*—Richard L. Raymond
*Attorney, Agent, or Firm*—Renner, Kenner, Greive, Bobak, Taylor & Weber

[57] ABSTRACT

A pharmaceutical composition of matter for delivering nitric oxide. The composition is an amine that was reacted with nitric oxide. The composition of matter is lipophilic and insoluble and therefore delivers nitric oxide to the specific area of the body where it is introduced. Also, a method of synthesizing an amine and reacting it with nitric oxide to form the pharmaceutical composition of matter. Finally, a method of using the pharmaceutical composition of matter to deliver nitric oxide to the body.

28 Claims, 6 Drawing Sheets

LIPOPHILIC POLYAMINE ESTERS FOR THE SITE SPECIFIC DELIVERY OF NITRIC OXIDE IN PHARMACEUTICAL USE

This application is a continuation-in-part of U.S. application Ser. No. 08/703,898 filed on Aug. 27, 1996, abandoned.

TECHNICAL FIELD

The present invention generally relates to nitric oxide releasing pharmaceutical compounds. More particularly, the present invention relates to pharmaceutical compositions that release nitric oxide under physiological conditions. Specifically, the present invention relates to pharmaceutical compounds that are biodegradable, lipophilic, insoluble amine esters that have been reacted with nitric oxide. The present invention also relates to a method for the synthesis of such amine esters, as well as the use of such compositions in pharmaceutical applications.

BACKGROUND OF THE INVENTION

Recent research has discovered the ubiquitous synthesis and use of nitric oxide (NO) throughout the biological systems of animals. For example, NO has been found to play a role in blood pressure regulation, blood clotting, neurotransmission, smooth muscle relaxation, and immune systems. For example, within the immune system, NO is believed both to inhibit key metabolic pathways, thereby inhibiting tumor growth, and to serve as an outright toxin that can be used to kill cells.

Furthermore, NO has been found to be a potent vasodilator within the bronchial circulation system of the lungs and is believed to play an important role in regulating pulmonary circulation. NO is also believed to relax the muscles within lung airways, thereby regulating breathing.

It is thus believed that the insufficient production of NO within various biological functions results in deleterious effects as manifested in various immune deficiencies, asthma, bacterial infections, impotence, and high blood pressure, to name a few. From a pharmacological standpoint, the delivery of NO to the body may serve as a remedy for ailments caused by the insufficient production of NO within the body.

Nitric oxide, however, as it is used within the enumerable biological functions of animals, is highly controlled and regulated because excess amounts of NO can be hazardous to living animals. For example, the introduction of NO into the blood stream can cause the irreversible lowering of blood pressure, ultimately leading to death. Thus, the introduction of NO into the body is not the simple solution to the effects caused by insufficient NO production within the body.

There are known pharmaceutical compositions capable of delivering NO. Namely, Keeffer et al, U.S. Pat. No. 5,039,705, teaches pharmaceutical compositions of the formula wherein $R_1$ and $R_2$ are independently chosen from straight chain and branched chain alkyl groups of 1 to 12 carbon atoms or benzyl, with the proviso that no branch occur on the alpha carbon of the alkyl groups, or $R_1$ and $R_2$ together with the nitrogen atom they are bonded to form a pyrrolidino, piperidino, piperazino or morpholino ring, $M^{+x}$ is a pharmaceutically acceptable cation, wherein x is the valence of the cation. Because this particular compound is a salt, the preferred method of administering this compound to animals is through injection into the bloodstream. It is also noteworthy that this particular compound is highly soluble in biological fluids thereby quickly releasing the NO which is loaded to the molecule.

Also, Keeffer et al, U.S. Pat. No. 5,366,997, teaches a similar pharmaceutical composition of the formula wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight olefinic and $C_{3-12}$ branched chain olefinic which are unsubstituted or substituted with hydroxy, alkoxy, acyloxy, halo or benzyl. $R_1$ and $R_2$ can also comprise various heterocyclic ring molecules as described therein.

It should be appreciated that the molecules as taught by Keeffer et al are soluble within body fluids. Chemistry dictates as much, as do the teachings of Keeffer et al as it is recommended to administer these drugs intravenously. It should further be appreciated that upon the intravenous introduction of these chemicals to a living animal, NO will be introduced throughout the body as the soluble compound disseminates throughout the body. As discussed above, unwarranted or overexposure of NO can have many harmful effects on living animals.

Thus, there is a need for a pharmaceutical composition capable of the site specific delivery of NO within living animals.

SUMMARY OF THE INVENTION

It is, therefore, a primary object of the present invention to provide a pharmaceutical composition of matter that releases nitric oxide under physiological conditions.

It is another object of the present invention to provide a pharmaceutical composition of matter that releases nitric oxide to the specific area within the body where it is introduced without disseminating uncontrollably throughout the body.

It is yet another object of the present invention to provide a pharmaceutical composition of matter that releases nitric oxide, and following the release of nitric oxide preferably biodegrades into naturally occurring compounds.

It is yet a further object of the present invention to provide a pharmaceutical composition of matter that releases nitric oxide whereby the rate of release is preferably slowed to provide extended nitric oxide dosage.

At least one of the foregoing objects of the present invention, together with the advantages thereof over existing pharmaceutical compositions which shall become apparent from the specification that follows, are accomplished by the invention as hereinafter described and claimed.

In general, the present invention provides a pharmaceutical composition of matter that releases nitric oxide when introduced to physiological mediums comprising: a NONOate, wherein the NONOate is insoluble in physiological mediums.

The present invention also provides a method of synthesizing a NONOate comprising the steps of: reacting an acyl chloride with an alcohol to form an acrylate; reacting the acrylate with an amine having at least one terminal amine group to form an amine ester derivative; and reacting the amine ester derivative with nitric oxide to form a NONOate.

The present invention further provides a method of providing nitric oxide to a specific area of the body comprising the step of delivering a composition of matter to a specific area of the body, the composition of matter comprising a NONOate, wherein the NONOate is insoluble in physiological mediums.

PREFERRED EMBODIMENT FOR CARRYING OUT THE INVENTION

The present invention is directed to a composition of matter that includes molecules that are nitric oxide (NO) donors; that is, molecules that release NO. Specifically, these molecules are amines that have been reacted with NO produce a molecule of the general formula (I)

(I)

wherein $R_1$ and $R_2$ are organic radicals, including nitrogen containing organic radicals. It should be appreciated that the molecule of formula (I) is an anion that is typically electronically balanced with a pharmaceutically acceptable cation to produce a stable compound or salt. Such salts are similar to those disclosed in U.S. Pat. No. 5,039,705, which is incorporated herein by reference. Pharmaceutically acceptable cations refer to non-toxic cations, which are well known to those of skill in the art.

For purposes of this disclosure, those amine molecules that have been reacted with NO will be referred to as having NO loaded thereto. Heretofore in the art, those amine molecules having NO loaded thereto, as generally represented by formula (I), as well as the general NONOate formulas hereinafter described, have been referred to as 1-Substituted Diazen-1-ium -1,2-Diolates, or NONOates. Thus, the NO donor molecules of the present invention are NONOates.

Previously known NONOates, however, are soluble in physiological mediums, and thus disseminate throughout the body once introduced therein. The NONOates of the present invention, however, are insoluble in physiological mediums. Thus, upon introduction into the body, the molecules will not rapidly be distributed throughout the body allowing for the site specific delivery of NO. For purposes of this disclosure, physiological mediums will refer to those environments found within the bodies of animals, particularly humans. Thus, physiological mediums will include aqueous mediums.

It has been found that the characteristic of insolubility derives from the chemical nature of the NONOate, and more particularly from the size and/or substituents of one or both of the organic radical groups $R_1$ or $R_2$ as represented in formula (I). The size of the organic radical group refers to the number of carbon atoms therein. Obviously, where $R_1$ or $R_2$ is hydrogen, the complementary organic radical group should be sufficiently large to compensate for the lack of carbon atoms and render the molecule insoluble. Thus, the organic radical groups $R_1$ and/or $R_2$ should be sufficiently large to render the molecule represented by formula (I) insoluble. One of ordinary skill in the art, without undue experimentation, should be able to readily determine the necessary size of each organic radical group that will ultimately render the molecule insoluble. Although it should be appreciated that the size of each organic radical group can fluctuate based on the size of the other organic radical groups within the NONOate, the NONOate, as represented in formula (I), is typically rendered insoluble with a total of 8 carbon atoms, preferably with more than 10 total carbon atoms and most preferably with more than 12 total carbon atoms. Further, each organic radical group typically contains more than 2 carbon atoms and less than 20 carbon atoms, except in the case where a steroid radical is employed. For purposes of this disclosure, steroids can include any polycyclic compound having a fused reduced 17-carbon atom ring system, such as cyclopentanoperhydrophenanthrene.

It is also preferred that the NONOates of the present invention biodegrade following the release of NO, as will hereinafter be described. Even more preferably, the NONOates of the present invention should biodegrade into substances that are naturally produced or naturally found within the biological systems of animals. For example, the presence of an ester of a carboxylic acid in one or both of the $R_1$ or $R_2$ groups of formula (I) will allow the molecule to biodegrade upon hydrolysis yielding a carboxylic acid and an alcohol. A NONOate having an ester of a carboxylic acid according to the present invention is represented by the formula (II)

(II)

wherein $R_2$ and $R_3$ are organic radical groups, such as straight and branched chain alkyl and alkenyl groups containing 2 to 20 carbon atoms, and steroidal groups, and wherein $R_4$ is hydrogen or an organic radical group, such as a straight alkyl group containing 2 to 6 carbon atoms. These organic radical groups can include nitrogen containing organic radicals. As with the NONOate represented by formula (I), the NONOate represented by formula (II) should contain a combination of organic radical groups that are large enough to render the molecule insoluble. As with the NONOate of Formula (I), one of skill in the art, without undue experimentation, should be able to determine the size of each organic radical group necessary to render the NONOate insoluble. Typically, a molecule as represented by formula (II) is rendered insoluble with 12 total carbon atoms, and more preferably with 14 carbon atoms. Preferably, this is achieved when $R_4$ contains between 2 and 3 carbon atoms and $R_2$ and $R_3$ contain between 2 and 20 carbon atoms or steroid radicals. An exemplary compound represented by formula II is alkyl methyl glycine NONOate, wherein the organic radicals of formula II are as follows: $R_2$ and $R_3$ are straight or branched chain alkyl or alkenyl groups containing 2 carbon atoms, and $R_4$ is a straight chain alkyl group, such as lauryl, or a steroidal, such as cholesterol or phytol.

Like the molecule represented by formula (I), the NONOate of formula (II) is anionic and thus should be associated with a pharmaceutically acceptable cation to create an electronically stable molecule or salt. It should be appreciated that a pharmaceutically acceptable cation can include a protonated amine or polyamine molecule, including amines similar to the amine to which the NO is loaded to form the NONOate of formulas (I) and (II). The salt resulting from the relationship between the pharmaceutically acceptable cation and the anion of the present invention is also referred to as an intermolecular salt. These intermolecular salts can comprise the pharmaceutical composition of matter of the present invention.

In another preferred embodiment of the present invention, the molecules that form the composition of the present invention are polyamines that contain at least two amine groups that have been reacted with NO to produce a molecule of the general formula (III)

(III)

wherein $R_5$ is an organic radical, such as straight and branched alkyl and alkenyl groups containing 1 to 20 carbon atoms, $R_6$ is an organic radical group, such as straight and branched chain alkyl groups containing 2 to 6 carbon atoms, and $R_7$ is hydrogen or an organic radical, such as straight and branched alkyl or alkenyl groups containing 1 to 20 carbon atoms. The organic radical groups $R_5$ and $R_7$ can include nitrogen containing organic radical groups. The size and/or substituents of the organic radical groups of formula (III) should be large enough to render the molecule insoluble. Particularly, the size of at least one of the organic radical groups $R_5$, $R_6$ or $R_7$ should be sufficiently large so as to render the molecule insoluble in physiological mediums. Typically, this includes a total of at least 12 carbon atoms, preferably at least a total of 14 carbon atoms and more preferably at least a total of 16 carbon atoms. Preferably $R_{10}$ contains between 2 and 6 carbon atoms and $R_5$ and $R_7$ contain between 1 and 20 carbon atoms, and may include more where a steroid radical is employed. An exemplary compound represented formula III is monoalkyl putrescine NONOate, wherein the organic radicals of formula III are as follows: $R_5$ is an alkyl group, $R_6$ is a 4 carbon atom straight or branched chain alkyl group and $R_7$ is a hydrogen atom.

It should be appreciated that the preferred molecules of the present invention represented by formula (III) are zwitterions, which are molecules whose net charge is zero. Therefore, whereas monoamines are typically associated with a pharmaceutically acceptable cation to form a salt, the zwitterion is typically not associated with another molecule in a similar relationship. Nonetheless, while the preferred molecular structure for the polyamine NONOates of the present invention is that of a zwitterion, it is noted that polyamine NONOates can form intermolecular salts with cations including protonated polyamines similar to the polyamine to which NO is loaded to form the NONOate. Thus, while it is preferred that the pharmaceutical composition of matter of the present invention include polyamine zwitterion NONOates, it can also include polyamine intermolecular salt NONOates. It should be appreciated that a more efficient delivery of NO can be achieved with the zwitterion NONOate. Zwitterion NONOates deliver twice the NO inasmuch as intermolecular salts require two polyamine molecules to deliver two NO molecules and zwitterions only require one polyamine molecule to deliver two NO molecules.

Figure 1:
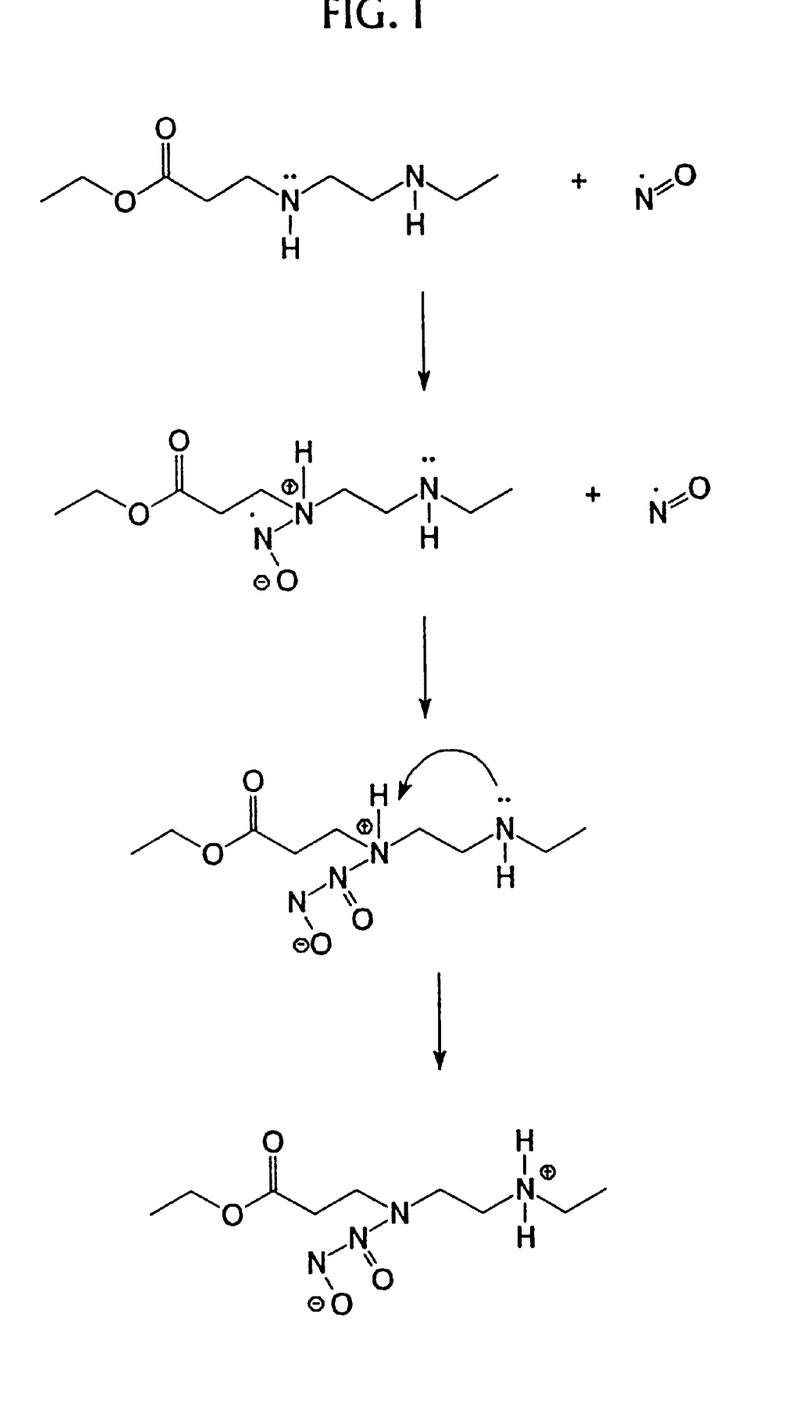
FIG. 1 is the mechanism believed to represent NONOate formation by the step wise addition of nitric oxide.
Figure 2:
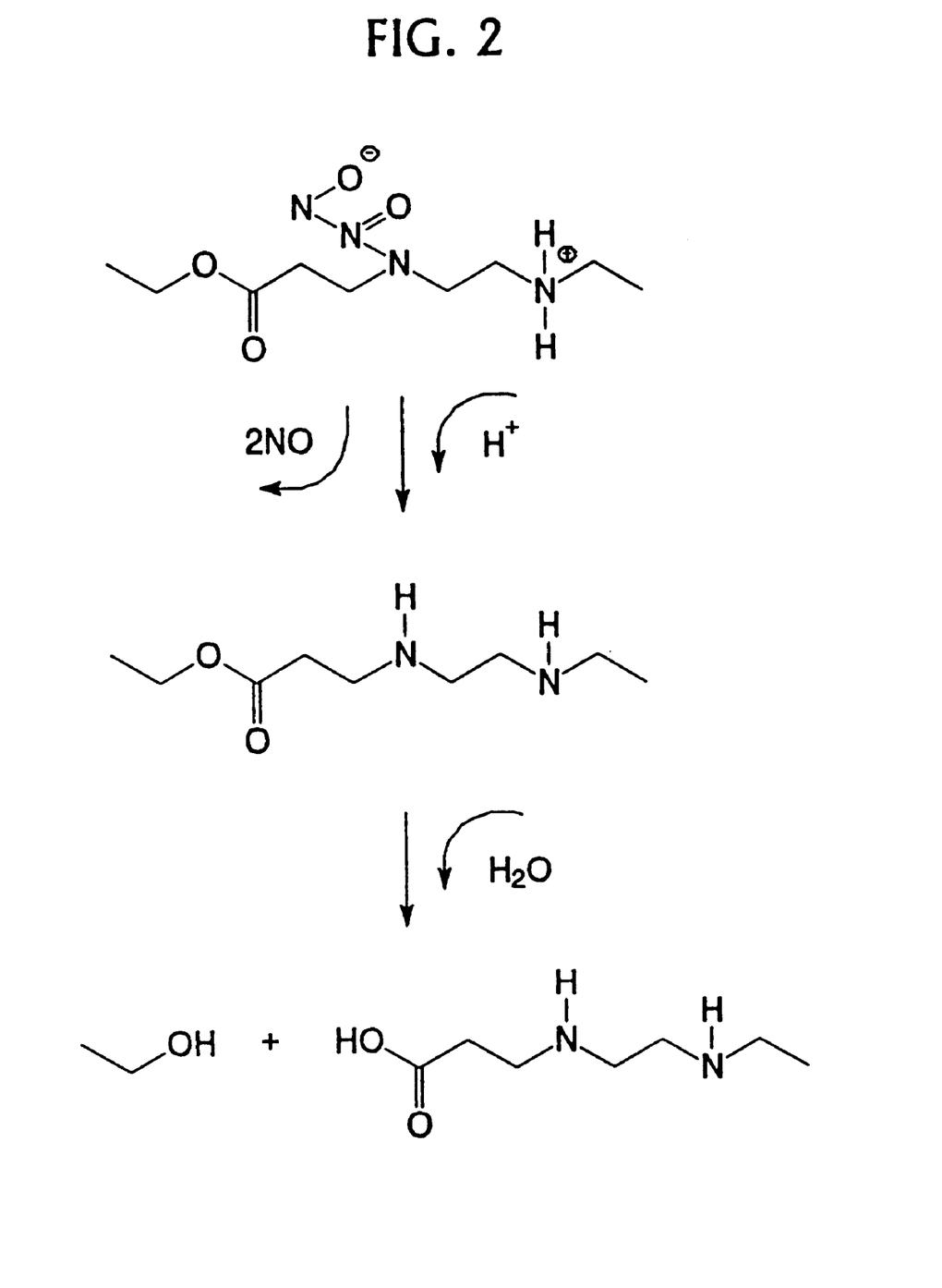
FIG. 2 is the mechanism believed to represent the spontaneous release of nitric oxide from a lipophilic NONOate followed by the spontaneous decomposition of the polyamine ester.
Figure 3:
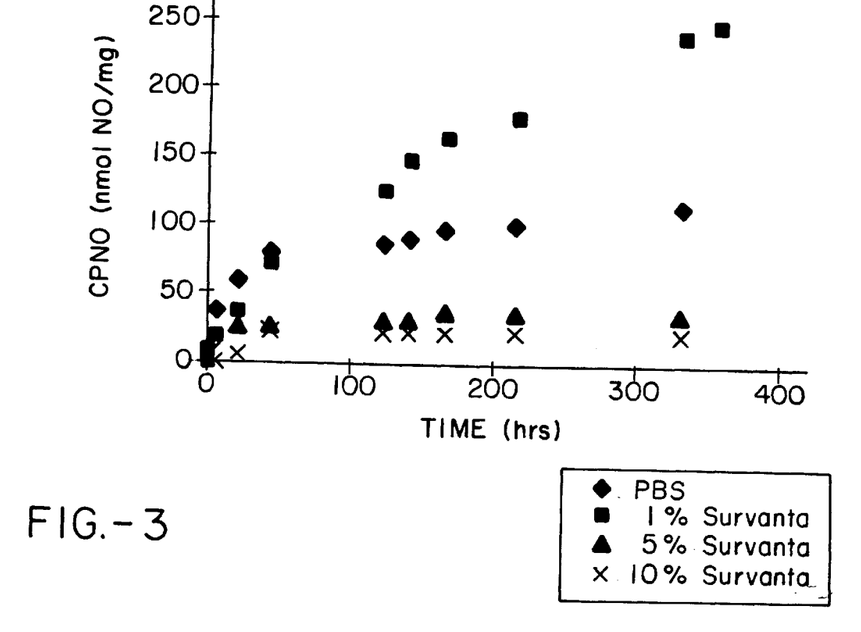
FIG. 3 is a release profile for Cholesterylputreanine-NONOate in PBS, 1% Survanta, 5% Survanta and 10% Survanta.
Figure 4:
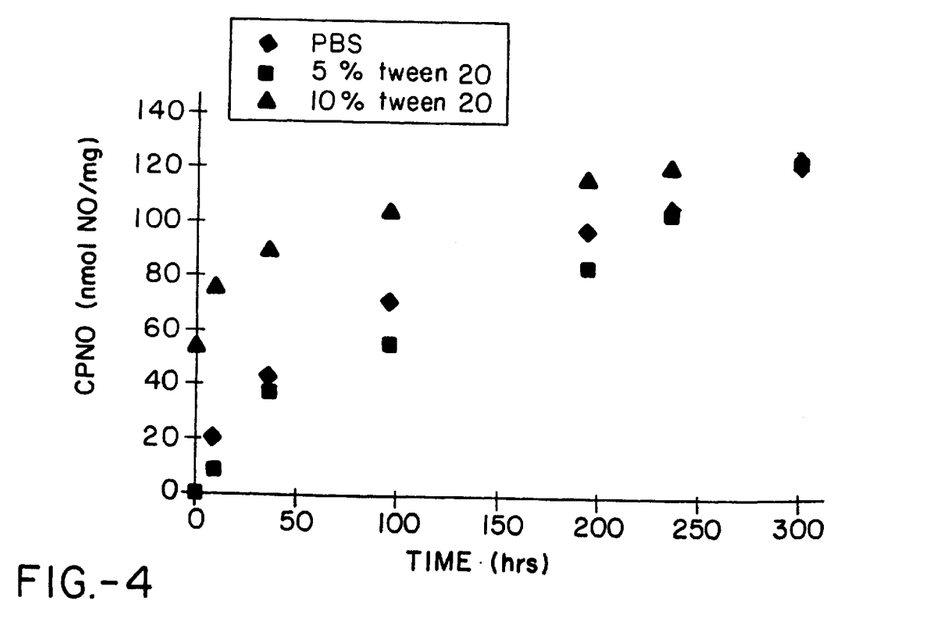
FIG. 4 is a release profile for Cholesterylputreanine-NONOate in PBS, 5% Tween 20, and 10% Tween 20.
Figure 5:
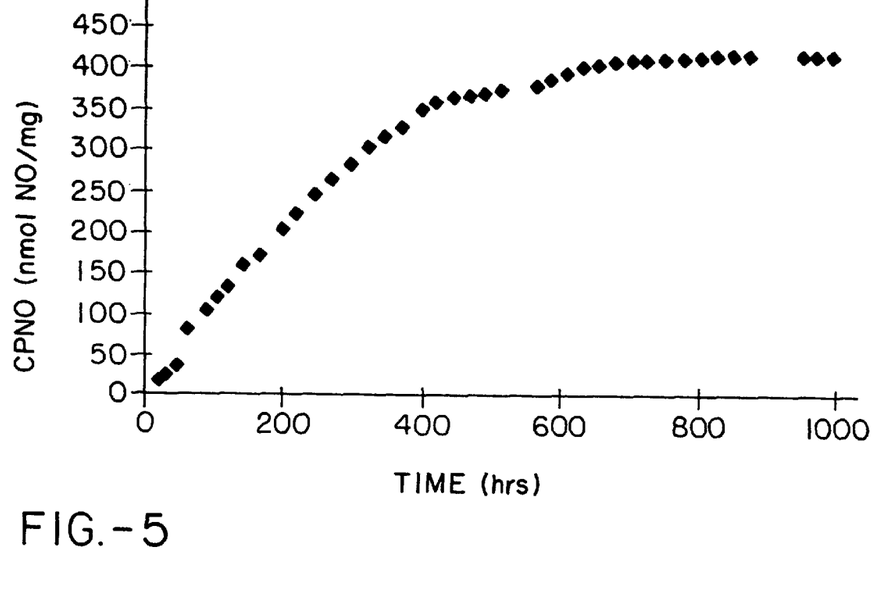
FIG. 5 is a release profile for Cholesterylputreanine-NONOate in PBS with 10% Tween 80 at pH 2.0.
Figure 6:
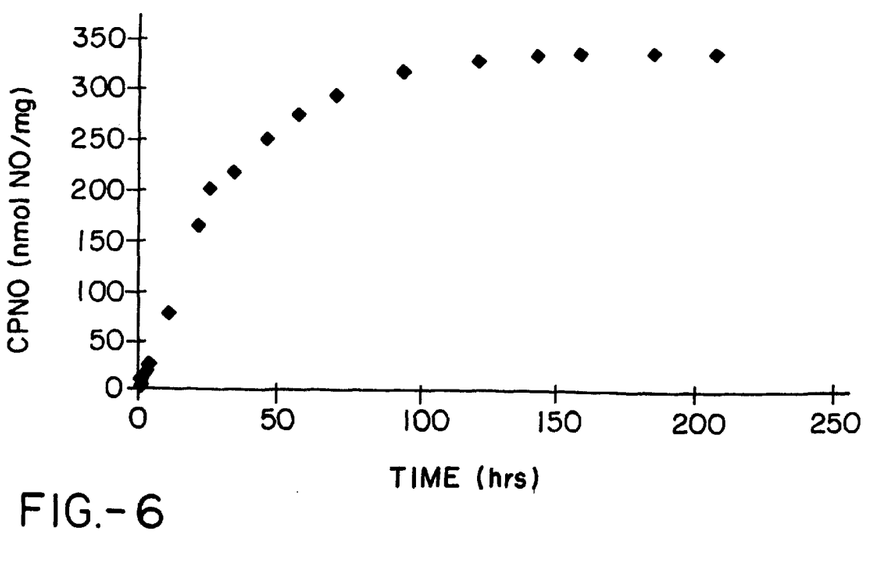
FIG. 6 is a release profile for Cholesterylputreanine-NONOate in THF pH at 1.0.
Figure 7:
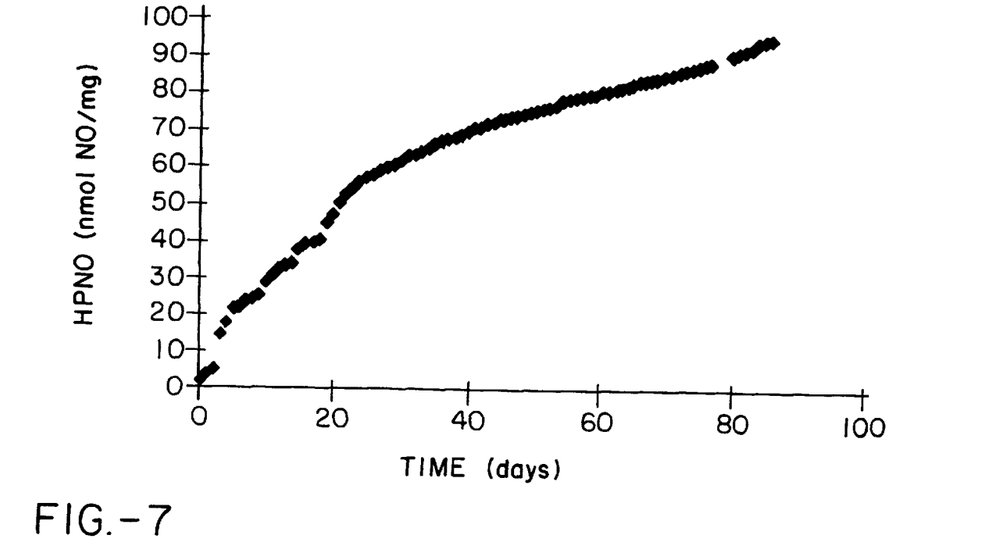
FIG. 7 is a release profile for Dicholesterylspermate-NONOate in PBS.
Figure 8:
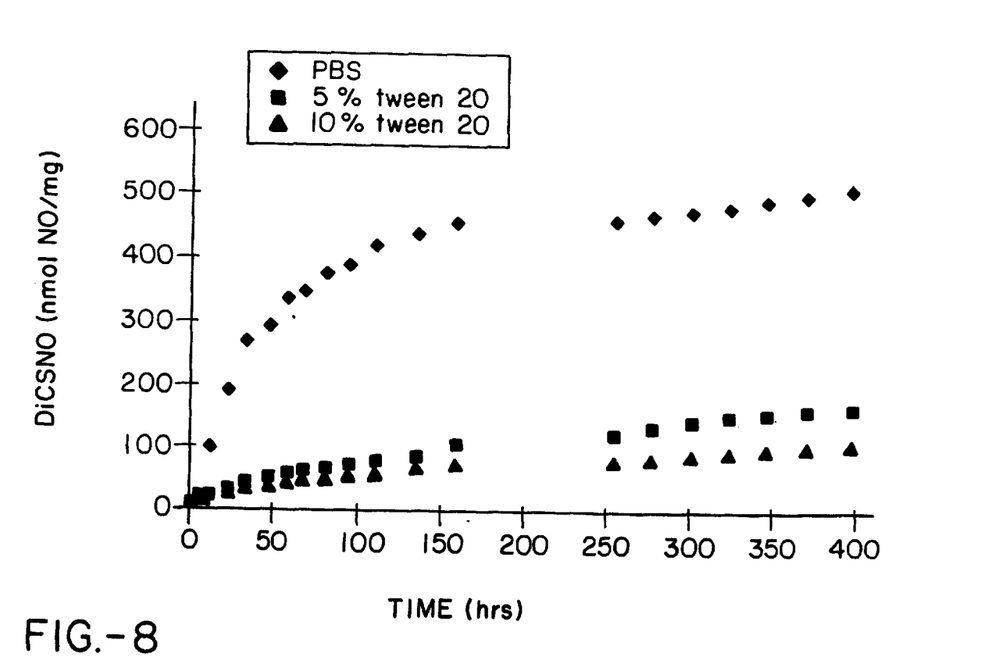
FIG. 8 is a release profile for Hexadecanylputreanine-NONOate in PBS, 5% Tween 20, and 10% Tween 20.
Figure 9:
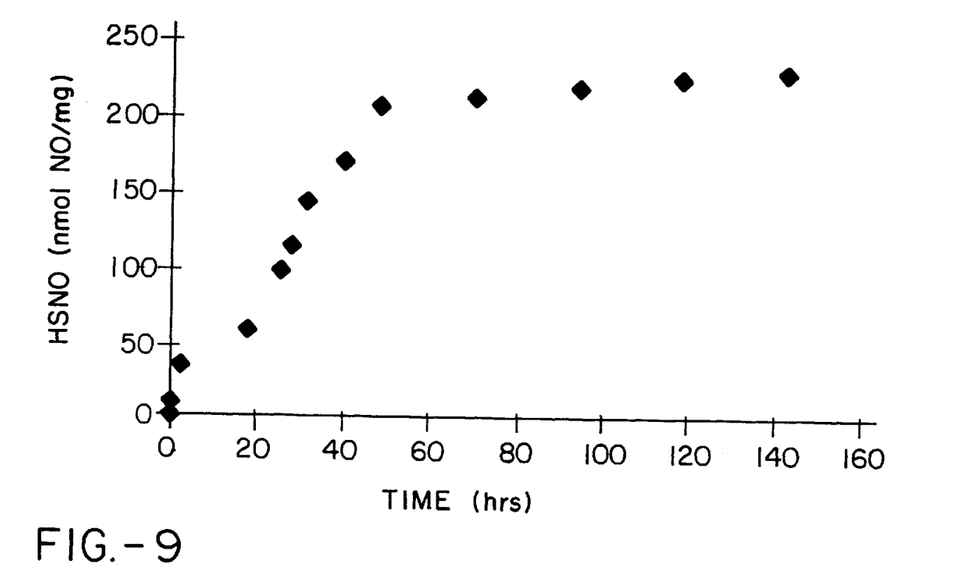
FIG. 9 is a release profile for Dihexadecanylspermate-NONOate in THF at pH 1.0; and, FIG. 10 is a release profile for Dihexadecanylspermate-NONOate in PBS and 1% Survanta.
Figure 10:
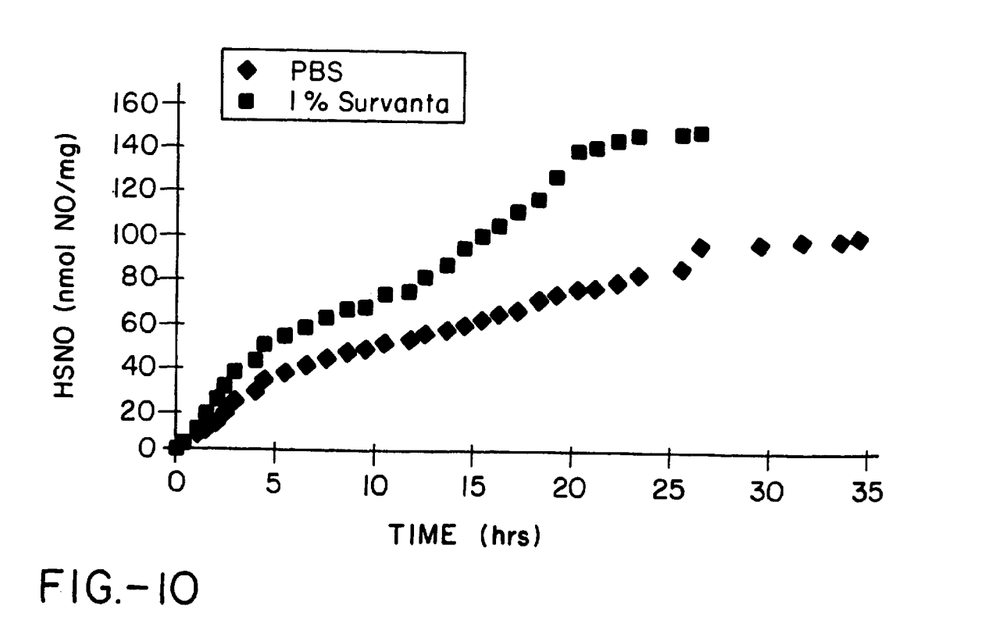

Without wishing to be bound to any particular theory, the formation of a zwitterion NONOate is represented in FIG. 1. It is further believed that nitric oxide is released from the NO donor molecules the present invention according to the mechanism as generally represented in FIG. 2. It should therefore be appreciated that the present invention embodies the lipophilic, insoluble, biodegradable NO donor molecules as hereinafter described, as well as the lipophilic, insoluble biodegradable amines and polyamines to which NO is loaded to yield the NO donor molecules as hereinafter described.

It is further preferred that the polyamine NONOates of the present invention biodegrade and preferably degrade into substances that are naturally produced or naturally found within the biological systems of animals. The biodegradability of the NONOates of the present invention preferably results from the presence of an ester linkage within one or both of the organic radical groups defined as $R_5$ or $R_7$ in formula (III). More preferably, one or both organic radical groups defined by $R_5$ or $R_7$ contain an ester of a carboxylic acid, which when hydrolyzed yields a carboxylic acid and an alcohol.

Thus, in this preferred embodiment where the polyamine NONOate contains an ester of a carboxylic acid, the preferred molecule of the present invention is defined according to the general formula (IV)

(IV)

(V)

wherein $R_6$ is an organic radical group, such as straight and branched chain alkyl groups containing 2 to 6 carbon atoms, $R_7$ can be a hydrogen atom, or an organic radical group, such as straight and branched chain alkyl and alkenyl groups containing 1 to 20 carbon atoms, $R_8$ is an organic radical group, such as straight or branched chain alkyl, alkenyl and steroidal groups containing 2 to 20 carbon atoms, and $R_9$ is an organic radical group, such as a straight chain alkyl group containing 2 to 4 carbon atoms. The $R_6$ and $R_9$ organic radicals preferably include aliphatics, and $R_7$ and $R_8$ can include nitrogen containing organic radicals. The nitrogen containing organic radicals of $R_7$ or $R_8$ preferably contain less than 20 carbon atoms. For example, $R_7$ can include a spermidine radical. An exemplary compound represented by formula IV is alkyl putreanine NONOate, wherein the organic radicals of formula IV are as follows: $R_6$ is a straight chain alkyl or alkenyl group containing 4 carbon atoms, $R_7$ is a hydrogen atom, $R_8$ is a straight chain alkyl group, such as ethyl, butyl, lauryl and the like, a steroidal group, such as cholesterol and the like, an alkenyl group, such as oleyl and the like, or branched chain alkyl group, such as phytol and the like, and $R_9$ is a straight chain alkyl group containing 2 carbon atoms.

As with the molecules of the present that are explained hereinabove, the number of carbon atoms within at least one of the organic radical groups should be large enough to render the molecule represented by the formula (III) insoluble in physiological mediums. It should be appreciated that the necessary size of any given organic radical group is a function of the size of the other radical groups because the overall size of the molecule is typically determinative of the solubility of the molecule. Again, one of skill in the art should readily be able to determine the necessary size of each organic radical to render the molecule insoluble without undue experimentation.

Accordingly, with the goal of rendering the molecule defined by formula (IV) water insoluble, the following is preferred: $R_6$ is an organic radical having at least 2 carbon atoms; $R_7$ is hydrogen or an organic radical having at least one carbon atom; $R_9$ is an organic radical having at least 1 carbon atoms; and $R_8$ is an organic radical having at least 9 carbon atoms. More preferably, $R_6$ includes between 2 and 6 carbon atoms, $R_7$ is hydrogen or an organic radical having between 1 and 6 carbon atoms; $R_9$ is an organic radical having between 1 and 3 carbon atoms; and $R_8$ is an organic radical having between 9 and 20 carbon atoms or a steroid radical.

In yet another preferred embodiment, the $R_7$ organic radical group of formula (IV) includes an ester of a carboxylic acid. When this is the case, the molecule of the present invention is defined according to the general formula (V)

wherein $R_6$ is an organic radical group, such as a straight and branched chain alkyl group containing 2 to 6 carbon atoms, $R_9$ and $R_{10}$ are organic radicals, such as straight chain alkyl groups containing 2 to 4 carbon atoms, and $R_8$ and $R_{11}$ are organic radical groups, such as straight and branched chain alkyl, alkenyl and steroidal groups. The $R_6$, $R_9$, and $R_{10}$ organic radicals preferably include aliphatics and the $R_8$ and $R_{11}$ organic radical groups can include nitrogen containing organic radicals.

At least one of the organic radicals $R_6$, $R_4$, $R_8$, $R_{10}$ and $R_{11}$ should be of sufficient size so as to render the molecule insoluble in physiological mediums. Again, it should be appreciated that the given size of any one organic radical group will be a function of the size and/or chemical makeup of the other organic radical groups. It is, however, preferred that the organic radical $R_6$ contain at least 2 carbon atoms, and more preferably contain between 2 and 6 carbon atoms; the organic radicals $R_9$ and $R_{10}$, which can be the same or different, contain at least one carbon atom, and more preferably contain between 1 and 2 carbon atoms; the organic radicals $R_8$ and $R_{11}$, which can be the same or different, contain at least 2 carbon atoms, and more preferably contain between 2 and 20 carbon atoms, or contain steroid radicals. An exemplary compound represented by formula V is dialkyl spermate NONOate, wherein the organic radicals of formula V are as follows: $R_6$ is a straight or branched chain alkyl group containing 4 carbon atoms, $R_8$ and $R_{11}$ are alkyl groups, such as ethyl, butyl and lauryl, and $R_9$ and $R_{10}$ are straight chain alkyl groups containing 2 carbon atoms.

As previously stated, it is preferred that the NO donor molecules of the present invention hydrolyze and yield a carboxylic acid and an alcohol. Accordingly, the carboxylic acid will preferably contain a polyamine functionality, and the alcohol, for example, will be that which is derived from the $R_8$ or $R_{11}$ organic radical groups when the molecule of formula (V) is hydrolyzed. Because the NO donor molecules of the present invention are for pharmaceutical use, the resulting carboxylic acids and alcohols preferably should not be hazardous to the health of animals. In a preferred embodiment of the present invention, hydrolysis of the NO donor molecule will yield a naturally occurring polyamine carboxylic acid and a naturally occurring alcohol. The term "naturally occurring" refers to those polyamine carboxylic acids and alcohols that are naturally present within the biological systems of animals.

Accordingly, the NO donor molecules of the present invention can hydrolyze into polyamine-carboxylic acids having the general formula (VI)

(VI)

wherein $R_{12}$ and $R_{13}$ are organic radicals, such as straight and branched chain alkyl groups containing 2 to 6 carbon atoms, $R_{14}$ is a hydrogen atom or an organic radical, such as straight and branched chain alkyl and alkenyl groups containing 1 to 6 carbon atoms. Preferably, $R_{12}$ contains at least one carbon atom, and more preferably contains between 1 and 3 carbon atoms; $R_{13}$ contains at least 2 carbon atoms, and more preferably contains between 2 and 6 carbon atoms; and $R_{14}$ is hydrogen or an organic radical having more than one carbon atom and more preferably between 1 and 6 carbon atoms. For example, the NO donor molecules of the present invention will hydrolyze into the naturally occurring polyamine-carboxylic acids of putreanine or isoputreanine. $R_{12}$ and $R_{13}$ are preferably aliphatic organic radicals, and $R_{14}$ can include nitrogen containing organic radicals. Exemplary compounds represented by formula VI are putreanine, wherein the organic radicals of formula VI are as follows: $R_{12}$ is a straight chain alkyl group containing 2 carbon atoms, $R_{13}$ is a straight or branched chain alkyl group containing 4 carbon atoms and $R_{14}$ is a hydrogen atom; and isoputreanine wherein the organic radical groups of formula VI are as follows: $R_{12}$ and $R_{13}$ are straight or branched chain alkyl groups containing 3 carbon atoms and $R_{14}$ is a hydrogen atom.

6 carbon atoms. An exemplary compound represented by formula VII is naturally occurring polyamine-dicarboxylic acid spermic acid, wherein the organic radicals of formula VII are as follows: $R_{12}$ and $R_{16}$ are straight chain alkyl groups containing 2 carbon atoms and $R_{13}$ is a straight chain alkyl group containing 4 carbon atoms.

The alcohols resulting from the hydrolysis of the molecules of the present invention can be any alcohol and is preferably those which are naturally found within the body. Preferred are aliphatic alcohols having from 2 to 20 carbon atoms, as well as sterol alcohols such as cholesterol.

For example, in one embodiment of the present invention, hydrolysis of an NO donor molecule of the present invention will yield the naturally occurring products of putreanine and cholesterol. This NO donor molecule is defined according to the general formula (VIII)

(VIII)

Further, the NO donor molecules of the present invention can hydrolyze into polyamine-dicarboxylic acids having the general formula (VII)

In another embodiment of the present invention, the NO donor molecule of the present invention will hydrolyze into ethanol and spermic acid. This NO donor molecule is defined according to the general formula (IX)

(IX (VII wherein $R_{12}$, $R_{13}$, and $R_{15}$ are organic radicals, such as straight chain alkyl groups containing 2 to 6 carbon atoms. Preferably, $R_{12}$ and $R_{15}$, which can be the same or different, contain at least one carbon atom, and more preferably include between 1 and 3 carbon atoms; $R_{13}$ contains at least 2 carbon atoms, and more preferably contains between 2 and Other examples of molecules according to the present invention that are capable of being reacted with NO to produce NO donor zwitterion molecules according to the present invention are represented in the subsequent discussion of Examples.

It should be appreciated that the term organic radical has been used herein to represent the fact that a number of substituents can be selected for the various R groups in the foregoing formulas without departing from the scope of the invention. Indeed, those atoms or substituents that are critical to the success and practice of the present invention have been specifically identified in the foregoing formulas. Also, the skilled artisan has been directed to those limitations, such as size, that are either required or desirable in practicing the present invention.

As used in the art, organic radical may also be referred to as an organic group, an organic moiety, a moiety, or a carbon-based group. Although the groups typically include carbon atoms, hetero atoms such as nitrogen or oxygen can be present within the various groups. In fact, a number of hetero atoms can be contemplated but are limited by their impact on the stability of the compound, their affect on the carrier that may be employed with the compound, and their affect on the body. These determinations can be made without undo experimentation.

In most situations, it is cost effective and synthetically easier to make and use compounds according to the present invention that have simple organic groups. These, of course, include alkyl and alkenyl groups, which generally fall under the category of aliphatic groups. These groups can be linear or branched, and where it is synthetically appropriate, they can be cyclic or acyclic. As noted herein, it has been useful to employ steroid radicals for certain groups. Steroid radicals have been defined to include any polycyclic compound that has a fused reduced 17-carbon atom ring system, such as cyclopentanoperhydrophenanthrene. The skilled artisan will be able to select a number of steroidal groups that can be useful.

Inasmuch as the compounds of the present invention are intended for pharmaceutical use, and it is highly desirable that they degrade into compounds naturally present within the body, the skilled artisan will appreciate that the organic groups may be more complex in some situations. Indeed, they can include lauryl groups, oleyl groups, phytol groups, or cholesterol groups, to name a few.

Accordingly, by selecting various organic radicals, a number of compounds can be made and used that fall within the teachings of this invention. Non-limiting examples of compounds include methyl glycine NONOate, putrescine NONOate, alkyl putreanine NONOate, dialkyl spermate NONOate, isoputreanine NONOate, cholesterylputreanine NONOate, dicholesterylspermate NONOate, hexadecanylputreanine NONOate, and dihexadecanylspermate NONOate.

As previously mentioned, the molecules of the present invention are NO donors, also referred to as NONOates. These NONOates release NO in aqueous environments at physiological pH. It has been observed that the release of NO from the NO donor molecules of the present invention is a function of both pH and solubility. Furthermore, it has been observed that the release of NO from the NO donor molecules of the present invention is a function of the terminal organic radical groups such as represented by $R_8$ and $R_{11}$ in the general formula (V). Without wishing to be bound to any particular theory, it is believed that certain terminal organic radical groups such as the $R_8$ or $R_{11}$ substituents shield the NONOate from solvent, thus allowing for a more sustained acid catalyzed release of NO. In other words, because the release of NO is a function of pH, i.e. NO release increases with acidity, it should be appreciated that the lipophilicity of the NO donor molecules of the present invention serve to regulate the NO release by maintaining the molecule in a non-aqueous environment, which is typically an environment where there is minimal contact with protons. With this understanding, the molecules of the present invention can be tailored to release NO at various rates depending on the lipophilicity of the molecule. It should further be appreciated that the lipophilicity and insolubility of the molecules of the present invention control the rate or degree that the NONOate molecules will disseminate throughout the body, thereby allowing for the site specific delivery of NO.

The present invention also embodies the synthesis of lipophilic, biodegradable amine molecules capable of being reacted with nitric oxide to form the NO donor molecules, or NONOates, as described in the foregoing discussion. Particularly, this method entails synthesizing the preferred NONOates of the present invention that include ester linkages, and more specifically the esters of carboxylic acids. Generally, this method comprises the reaction of an acyl chloride with an alcohol to form an ester of a carboxylic acid, or more specifically an acrylate. This acrylate is then reacted with a polyamine having at least one terminal primary amine group. The resulting polyamine ester derivative can be reacted with nitric oxide to form the zwitterion of the present invention. Accordingly, the molecules to which NO is loaded to form the NONOate molecules of the present invention will be referred to as polyamine ester derivatives. A more detailed discussion of the method of synthesis of the NO donor molecules of the present invention is found within the Examples of the present disclosure.

The molecules of the present invention are typically most useful when placed within a pharmaceutically acceptable carrier to form a pharmaceutical composition of matter. Those skilled in the art will be able to readily select a number of pharmaceutically acceptable carriers that can be employed without having deleterious impact upon the molecules. Non-limiting examples of suitable carriers include various aqueous solutions, creams, ointments, tablets, inhalers, and sprays. Specific examples of aqueous solutions include saline solution, lung surfactants, and mixtures thereof.

The present invention also embodies a method of delivering the NO donor molecules, or NONOates, of the present invention to specific areas within the body. It should be appreciated that a variety of delivery methods and/or systems can be employed to deliver NO to a specific area of the body, and such methods and/or systems are often dictated by the exact location within the body where NO is needed. For example, one such method can comprise placing the NO donor molecule of the present invention in an aqueous solution. Preferably, a surfactant is employed to form a suspension. The method would further comprise introducing this aqueous suspension into the lungs, such as through an inhaler, for the site specific delivery of NO to the bronchial airways. In this application, the use of the pharmaceutical lung surfactant Survanta®, available from Ross of Abbott Laboratories, Columbus, Ohio, would be preferred. It should be appreciated that the NO donor molecules will remain in the lungs inasmuch as the molecules are insoluble and will not enter the blood stream.

In another example, a method of delivering NO to desired body tissues and organs can comprise the direct application of the NO donor molecules dissolved or suspended in a solvent or liquid. More specifically, a common procedure in the repair of arteries includes grafting a synthetic tube to an artery to replace damaged tissue. It would be desirable to deliver NO to the area of fusion between the synthetic tube and the artery. Accordingly, an aqueous mixture or suspension of the NO donor molecules of the present invention could be employed and painted directly on the synthetic artery prior to grafting. Alternatively, the tube could be dipped in a mixture containing the NO donor molecules of the present invention. The mixture could employ solvents such as THF or ether, and such solvents would be evaporated prior to placing the tube within the body.

Still another example would entail topically delivering the NO molecules of the present invention. This would entail placing the NO donor molecules of the present invention in aqueous dispersion employing an appropriate level of surfactant. The mixture could then be applied topically via a spray, as a constituent within a topical cream, or as part of a pre-medicated bandage.

Yet another example entails placing the NO donor molecules of the present invention is a tablet for oral intake.

Such a delivery system would target the stomach and aid in the healing of such ailments as stomach ulcers. The bile salts encountered within the stomach would emulsify the tablet and bring the NO donor molecules of the present invention in contact with the acidic conditions within the stomach which would initiate and fully exhaust the NO release within the stomach.

In order to demonstrate a practice of the invention, NONOates as described hereinafter were prepared according to the concepts of the present invention. The examples disclosed herein should not be viewed as limiting the scope of the invention, the claims being determinative of the scope of the invention.

EXAMPLES

Synthesis of Cholesterylacrylate

Cholesterylacrylate was synthesized by dissolving 10 g of cholesterol in 50 ml of benzene. A 1.2 molar excess of acryloylchloride was added to the mixture and refluxed at 80° C. for 24 hours with stirring. The reaction mixture was allowed to cure to room temperature and the solvent removed by roto-evaporation in a room temperature water bath. The product was recrystallized twice using an ether/ethanol mixed solvent. The white solid product was isolated by vacuum filtration and dried in a room temperature vacuum oven for 18 hours. Cholesterylacrylate is represented by formula (X):

Synthesis of Hexadecanylacrylate

Hexadecanylacrylate was prepared by dissolving 10 g of hexadecanol in 50 ml of benzene. A 1.2 molar excess of acryloylchloride was added to the mixture and refluxed at 80° C. for 24 hours with stirring. The reaction mixture was allowed to cool to room temperature and the solvent was removed by roto-evaporation and room temperature water bath. The product was redissolved and 100 ml of diethyl ether and extracted five times with an equal volume of 10% NaHCO$_3$ in a separatory funnel. The ether fraction was isolated and the solvent was removed by roto-evaporation at room temperature followed by vacuum drying in a room temperature oven. Hexadecanylacrylate is represented by the formula (XI):

Synthesis of Cholesterylputreanine

Cholesterylputreanine (CP) was prepared by dissolving 2.0 g of cholesterylacrylate in 100 ml of THF which was then added dropwise to a five molar excess (2 g) of 1,4-diaminobutane in 50 ml of THF over an 18 hour period using an addition funnel with constant stirring by a magnetic stirrer. The reaction was stirred at room temperature for an additional four hours at which time the completion of the reaction was confirmed by H NMR. The cholesterylputreanine was separated from the diaminobutane by extraction into cold hexane, crystallized diaminobutane was separated by gravity filtration. The hexane was removed by roto-evaporation and vacuum oven dried at room temperature overnight. Cholesterylputreanine is represented by the formula (XII):

Synthesis of Dicholesterylspermate

Dicholesterylspermate (DiCS) was prepared by dissolving 2 g of cholesterylacrylate and 50 ml of THF which was added to a 0.05 molar amount of diaminobutane and 50 ml of THF over an 18 hour period using an addition funnel with constant stirring by a magnetic stirrer. The solvent was removed by roto-evaporation yielding a white precipitate. The solid was then dissolved in hexane and transferred to a separatory funnel. Residual diaminobutane was removed by extraction into acetonitrile which was performed in a total of three minutes. The hexane portion was subjected to roto-evaporation by subsequent drying in a vacuum oven at room temperature overnight. Dicholesterylspermate is represented by the formula (XIII):

Synthesis of Dihexadecanylspermate

Dihexadecanylspermate (DiHS) was prepared by dissolving 2.0 g of hexadecanylacrylate in THF and proceeding as described in Exhibit 4. Dihexadecanylspermate is represented by the formula (XV):

(XIII)

Synthesis of Hexadecanylputreanine

Hexadecanylputreanine (HP) was prepared by dissolving 2.0 g of hexadecanylacrylate in 100 ml of THF which was then added dropwise to a 4 molar excess of 1,4-diaminobutane and 50 ml of THF over an 18 hour period using an addition funnel with constant stirring by a magnetic stirrer. The reaction was stirred at room temperature for an additional four hours at which time the completion of the reaction was confirmed by NMR. The solvent was removed as described in Example 4 and the white solid product was washed with small amounts of acetonitrile. The product was then dissolved in hexane and added to a separatory funnel and extracted five times with acetonitrile as described in Example 4. The product was then isolated and characterized as described in Example 4. Hexadecanylputreanine is represented by the formula (XIV):

(XV)

(XIV)

Nitric Oxide Modification of the Molecules Synthesized in Examples

The polyamine ester derivatives synthesized above, including CP, DiCS, HP and DiHS, were modified with nitric oxide to form the following NONOates: Cholesterylputreanine-NONOate (CPNO); Dicholesterylspermate-NONOate (DiCSNO); Hexadecanylputreanine-NONOate (HPNO); Dihexadecanylspermate (DiHSNO); respectively. About 0.2 to about 0.5 grams of each of the polyamine ester derivatives synthesized above were dissolved in 80 ml of THF in a high pressure bottle equipped with a magnetic stir bar. The stirred mixture was purged with nitrogen gas and then purged with NO gas. The mixture was then brought to 70 psi of NO and left to react for 24 hours under continuous stirring. The reaction was purged with nitrogen gas and an aliquot was removed for U.V. analysis. The reaction was repeated until a maximum U.V. absorbance was achieved, which is indicative of complete NO loading to the polyamine ester derivative molecules. The NO gas was released, and the mixture was purged and flushed with nitrogen. The solvent was removed by roto-evaporation at room temperature followed by four hours in a vacuum oven set at room temperature. The sample containers were flushed with nitrogen gas and stored at −20° C. in a desiccator.

Nitric Oxide Release Profiles

Using a Monitor Labs Model 8440 Nitric Oxide Analyzer, interfaced with an HP 3396 A Chromatography Integrator, the nitric oxide release from the above synthesized NONOates was measured. The analyzer was connected to a release chamber consisting of an impinger bottle that had a one-way Teflon® stop cock valve attached in order to prevent the escape of any generated nitric oxide. Teflon® flow meters were inserted at the beginning of the circuit just before entry into the analyzer, and a helium tank with regulator was connected to the first flow meter.

The release profile was performed by adding about 3 to about 8 mg of the NO donor molecules prepared above to 25 ml of phosphate-buffered saline (PBS) (pH 7.4) in an impinger bottle that was subjected to continuous stirring. Varying amounts of the lung surfactant Survanta was added to certain samples, as were the surfactants Tween® 20 and Tween® 80. Tween® is available from Fisher Scientific Company, Fair Lawn, N.J. Still in other examples, the NONOates were simply dissolved in THF. Although the NONOates are insoluble in aqueous solution, sonication pulverized the compound adequately to produce fine particles that increased the surface area of the compound allowing a suspension to form. Once the impinger bottle was assembled, it was held in a water sonicator bath and sonicated until the insoluble sample was pulverized into fine particles or an emulsion. The amount of liberated NO was determined by the daily or timely flushing of helium through the solution and into the analyzer. Typically, measurements were taken every 2–4 hours during the first 18 hours and then every 12 hours thereafter. Eventually, readings only needed to be taken every 24 hours as the end of the release profile was approached. Helium gas was flushed through the system at 12 psig and the first flow meter was set to 150 ml/min. The second flow meter was adjusted to allow maximum flow. The released data was then used to compile the release profiles represented in FIGS. 3–10. The release profiles as represented in FIGS. 3–10 depict NO release from the NONOates in nmol NO/mg NONOate versus time in hours.

Based on these release profiles, the half-life and % Release for each NONOate prepared above was calculated and is represented in Table I, which represents NO release in PBS at pH 7.4.

TABLE I

| Compound | half-life | % Release |
|---|---|---|
| CPNO | 60 hr | 3.4 |
| DiCSNO | 23 days | 4.9 |
| HPNO | 81 hr | 23 |
| DiHSNO | 7.1 days | 7.4 |

This table is representative of the affect that molecular weight has on the NO release, which for CPNO was about 3.4%, yielding a half-life of about 60 hours, for DiCSNO was about 4.9% yielding a half-life of about 23 days, for HPNO was about 23%, yielding a half-life of about 81 hours, and for DIHSNO was about 7.4% yielding a half-life of about 7.1 days.

The effect that the lung surfactant Survanta has on the release of NO from NONOates of the present invention is represented in Table II where the half-life and % Release of cholesterylputreanine-NONOate (CPNO) and dihexadecanylspermate-NONOate (DiHSNO) are represented.

TABLE II

| | PBS | | 1% Survanta | | 5% & 10% Survanta | |
|---|---|---|---|---|---|---|
| Compound | half-life | % Release | half-life | % Release | half-life | % Release |
| CPNO | 60 hr | 3.4 | 62 hr | 7.4 | 39 hr | 1.1 |
| DiHSNO | 7.1 days | 7.4 | 8.9 days | 11 | no data | no data |

Based on the data represented in TABLE II, it is evident that the percent release increased in 1% Survanta®, while the half-life did not change substantially; the CPNO having a release of about 3.4% in PBS with a half-life of about 60 hours, and about 7.4% in 1% Survanta® with a half-life of about 62 hours; the DiHSNO having a release of about 7.4% in PBS with a half-life of about 7.1 days, and about 11% in 1% Survanta® with a half-life of about 8.9 days. When the concentration of Survanta® was raised to 5 and 10 percent, the results were similar with decreased percent release and shortened half-life; the CPNO having a release of about 1.1% with a half-life of about 39 hours. No data was obtained for DiHSNO.

Table III similarly demonstrates the affect that the surfactant Tween 20 has on the NO release of cholesterylputreanine-NONOate (CPNO) and hexadecanylputreanine-NONOate (HPNO) as represented in half-life and % Release.

TABLE III

| | PBS | | 5% Tween | | 10% Tween 20 | |
|---|---|---|---|---|---|---|
| Compound | half-life | % Release | half-life | % Release | half-life | % Release |
| CPNO | 60 hr | 3.4 | 104 hr | 3.6 | 72 hr | 3.7 |
| HPNO | 81 hr | 9.5 | 89 hr | 7.1 | 108 hr | 2.0 |

For CPNO, little change was observed in percent release as the surfactant concentration was raised to 10%; the percent release in PBS was about 3.4%, in 5% Tween® was about 3.6%, and in 10% Tween® was about 3.7%. The half life increased in 5% Tween® and decreased in 10% Tween®; in PBS, the half-life of CPNO was about 60 hours, in 5% Tween® was about 104 hours, and in 10% Tween® was about 72 hours. With HPNO, however, the percent release was about 9.5% in PBS with a half-life of about 81 hours, about 7.1% in 5% Tween® with a half-life of about 89 hours, and about 2.0% in 10% Tween® with a half-life of about 108 hours.

Finally, the affect that THF at pH 1.0 has on the NO release of cholesterylputreanine-NONOate (CPNO) and dihexadecanylspermate-NONOate (DiHSNO) is presented in terms of half-life and % Release in Table IV.

TABLE IV

| Compound in THF pH 1 | half-life | % Release |
|---|---|---|
| CPNO | 21 hr | 20 |
| DiHSNO | 24 hr | 17 |

As is represented in TABLE IV, at a pH of 1, the percent release of CPNO was about 20% with a half-life of about 21 hours, and for DiHSNO was about 17% with a half-life of about 24 hours.

It should be understood that the NO donor molecules of the present invention are an improvement over the existing art, as are the methods of synthesizing such NO donor molecules and the methods of delivering such NO donor molecules to specific sites within the body. It should also be appreciated that the NO donor molecules of the present invention can be used in a multitude of pharmaceutical uses wherein the delivery of NO is desired.

Based upon the foregoing disclosure, it should now be apparent that the NO donor molecules, methods of synthesizing NO donor molecules, and methods of employing the NO donor molecules to deliver NO to specific sites within the body as described herein will carry out the objects of the invention set forth hereinabove. It is, therefore, to be understood that any obvious variations fall within the scope of the claimed invention and thus, the selection of specific constituent and substituents can be determined without departing from the spirit of the invention herein disclosed and described. In particular, the NO donor molecules according to the present invention are not necessarily limited to those as set forth in the Examples. Moreover, as noted hereinabove, a variety of acrylyl and polyamine compounds could be employed in the synthesis of the molecules of the present invention but the starting materials which are preferred and which are specifically represented in this specification are chosen based on their ability to generate a product capable of decomposing into natural products. Furthermore, it should also be appreciated that, while preferred, the invention should not be limited to constituents that hydrolyze and yield carboxylic acids and naturally occurring alcohols. Thus, the scope of the invention shall include all modifications and variations that may fall within the scope of the attached claims.

Inasmuch as this specification is a continuation-in-part of U.S. Ser. No. 08/703,898, which was filed on Aug. 27, 1996, the entire contents of U.S. Ser. No. 08/703,898 is incorporated herein by reference.

We claim:

1. A NONOate compound that releases nitric oxide when introduced to physiological mediums, where said NONOate is defined by the formula (II)

(II)

wherein $R_2$ is selected from the group consisting of hydrogen, organic radicals having between 2 and 20 carbon atoms, and steroid radicals, $R_3$ can be selected from the group consisting of organic radicals having between 2 and 20 carbon atoms and steroid radicals, and $R_4$ is selected from the group consisting of organic radicals having between 2 and 3 carbon atoms, wherein said NONOate is insoluble in physiological mediums, and wherein said NONOate defined by formula (II) is electronically balanced with a pharmaceutically acceptable cation.

2. A pharmaceutical composition of matter that releases nitric oxide when introduced to physiological mediums comprising a molecule defined by formula (II), as set forth in claim 1, and a pharmaceutically acceptable carrier selected from the group consisting of aqueous solutions, creams, ointments, tablets, inhalers, and sprays.

3. A NONOate compound that releases nitric oxide when introduced to physiological mediums, where said NONOate is defined by the formula (III)

(III)

wherein $R_5$ is selected from the group consisting of organic radicals having between 1 and 20 carbon atoms, and steroid radicals, $R_6$ is selected from the group consisting of organic radicals having between 2 and 6 carbon atoms, and $R_7$ is selected from the group consisting of hydrogen, an organic radical having between 1 and 20 carbon atoms, and steroid radicals, wherein said NONOate is insoluble in physiological mediums.

4. A pharmaceutical composition of matter that releases nitric oxide when introduced to physiological mediums comprising a molecule defined by formula (III), as set forth in claim 3, and a pharmaceutically acceptable carrier selected from the group consisting of aqueous solutions, creams, ointments, tablets, inhalers, and sprays.

5. A compound that releases nitric oxide when introduced to physiological mediums, as set forth in claim 3, wherein $R_5$ is an ester of a carboxylic acid.

6. A compound that releases nitric oxide when introduced to physiological mediums, according to claim 3, wherein said NONOate is defined by the formula (IV)

(IV)

wherein $R_6$ is selected from the group consisting of organic radicals having between 2 and 6 carbon atoms, and steroid radicals, $R_7$ is selected from the group consisting of hydrogen, organic radicals having less than 20 carbon atoms, and steroid radicals, $R_8$ is an organic radical having less than 20 carbon atoms, and $R_9$ is selected from the group consisting of organic radicals having between 1 and 3 carbon atoms, and wherein said NONOate is insoluble in physiological mediums.

7. A pharmaceutical composition of matter that releases nitric oxide when introduced to physiological mediums comprising a molecule defined by formula (IV), as set forth in claim 6, and a pharmaceutically acceptable carrier selected from the group consisting of aqueous solutions, creams, ointments, tablets, inhalers, and sprays.

8. A compound that releases nitric oxide when introduced to physiological mediums, as set forth in claim 6, wherein $R_6$ contains at least 2 carbon atoms, $R_7$ is hydrogen or an organic radical having at least one carbon atom, $R_9$ contains at least 1 carbon atom and $R_8$ contains at least 9 carbon atoms.

9. A compound that releases nitric oxide when introduced to physiological mediums, as set forth in claim 8, wherein $R_8$ is a steroid.

10. A compound that releases nitric oxide when introduced to physiological mediums, as set forth in claim 3, wherein said NONOate is defined by the formula (V)

(V)

wherein $R_6$ is selected from the group consisting of organic radicals having between 2 and 6 carbon atoms, $R_9$ and $R_{10}$ are each independently selected from the group consisting of organic radicals having between 1 and 2 carbon atoms and $R_8$ and $R_{11}$ are each independently selected from the group consisting of hydrogen, organic radicals having between 2 and 20 carbon atoms and steroid radicals, and wherein said NONOate is insoluble in physiological mediums.

11. A pharmaceutical composition of matter that releases nitric oxide when introduced to physiological mediums comprising a molecule defined by formula (V), as set forth in claim 10, and a pharmaceutically acceptable carrier selected from the group consisting of aqueous solutions, creams, ointments, tablets, inhalers, and sprays.

12. A compound that releases nitric oxide when introduced to physiological mediums, as set forth in claim 10, wherein $R_6$ contains at least 2 carbon atoms, $R_9$ and $R_{10}$, which can be the same or different, contain at least one carbon atom, and $R_8$ and $R_{11}$, which can be the same or different, contain at least 2 carbon atoms.

13. A pharmaceutical composition of matter that releases nitric oxide when introduced to physiological mediums, as set forth in claim 1, wherein said NONOate biodegrades into an amine containing carboxylic acid and an alcohol.

14. A pharmaceutical composition of matter that releases nitric oxide when introduced to physiological mediums, as set forth in claim 13, wherein said amine-containing carboxylic acid and said alcohol are naturally found within the biological systems of animals.

15. A pharmaceutical composition of matter that releases nitric oxide when introduced to physiological mediums, as set forth in claim 13, wherein said NONOate biodegrades as a result of a hydrolysis reaction.

16. A compound that releases nitric oxide when introduced to physiological mediums, as set forth in claim 13, wherein said amine-containing carboxylic acid is defined by the formula (VI)

(VI)

wherein $R_{12}$ is an organic radical having between 1 and 3 carbon atoms and $R_{13}$ is an organic radical having between 2 and 6 carbon atoms, and $R_{14}$ is hydrogen or an organic radical having between 1 and 6 carbon atoms.

17. A pharmaceutical composition of matter that releases nitric oxide when introduced to physiological mediums comprising a molecule defined by formula (VI), as set forth in claim 16, and a pharmaceutically acceptable carrier selected from the group consisting of aqueous solutions, creams, ointments, tablets, inhalers, and sprays.

18. A pharmaceutical composition of matter that releases nitric oxide when introduced to physiological mediums, as set forth in claim 16, wherein said amine-containing carboxylic acid is selected from the group consisting of putreanine and isoputreanine.

19. A pharmaceutical composition of matter that releases nitric oxide when introduced to physiological mediums, as set forth in claim 13, wherein said amine-containing carboxylic acid is defined by the formula (VII)

(VII)

wherein $R_{12}$, $R_{13}$, and $R_{15}$ are organic radicals, each having between 1 and 3 carbon atoms and $R_{13}$ is an organic radical having between 2 and 6 carbon atoms.

20. A pharmaceutical composition of matter that releases nitric oxide when introduced to physiological mediums comprising a molecule defined by formula (VII), as set forth in claim 19, and a pharmaceutically acceptable carrier selected from the group consisting of aqueous solutions, creams, ointments, tablets, inhalers, and sprays.

21. A compound that releases nitric oxide when introduced to physiological mediums, as set forth in claim 19, wherein said amine-containing carboxylic acid is spermic acid.

22. A pharmaceutical composition of matter that releases nitric oxide when introduced to physiological mediums, as set forth in claim 13, wherein said alcohol is selected from the group consisting of aliphatic alcohols having from 2 to 20 carbon atoms and sterols.

23. The compound, as set forth in claim 6, wherein the organic radicals include nitrogen.

24. A method of synthesizing a NONOate comprising the steps of:
  reacting an acyl chloride with an alcohol to form an acrylate;
  reacting the acrylate with an amine having at least one terminal amine group to form an amine ester derivative; and
  reacting the amine ester derivative with nitric oxide to form a NONOate.

25. A method of providing nitric oxide to a specific area of the body comprising the step of delivering a composition of matter to a specific area of the body, the composition of matter comprising a NONOate, wherein the NONOate is insoluble in physiological mediums.

26. A method of providing nitric oxide to a specific area of the body, as set forth in claim 25, wherein the specific area of the body to be treated with nitric oxide is the bronchial airways, and wherein said step of applying comprises delivering an aqueous suspension of the NONOate through the use of an inhaler.

27. A method of providing nitric oxide to a specific area of the body, as set forth in claim 25, wherein the specific area of the body to be treated with nitric oxide in the stomach, and wherein said step of applying comprises delivering a pharmaceutical tablet comprising the NONOate to the stomach via ingestion.

28. A method of providing nitric oxide to a specific area of the body, as set forth in claim 25, wherein the NONOate is placed in a topical cream or ointment.

* * * * *